United States Patent [19]

Cleary

[11] Patent Number: 5,044,946
[45] Date of Patent: Sep. 3, 1991

[54] UNIVERSAL ORTHODONTIC ROTATION WEDGE

[75] Inventor: James D. Cleary, Glendora, Calif.

[73] Assignee: Minnesota Mining and Manufacturing Company, St. Paul, Minn.

[21] Appl. No.: 597,099

[22] Filed: Oct. 12, 1990

Related U.S. Application Data

[63] Continuation of Ser. No. 282,434, Dec. 8, 1988, abandoned.

[51] Int. Cl.⁵ .............................................. A61C 3/00
[52] U.S. Cl. ........................................ 433/18; 433/22
[58] Field of Search ...................... 433/18, 22, 11, 24

[56] References Cited

U.S. PATENT DOCUMENTS

| | | | |
|---|---|---|---|
| 3,758,947 | 9/1973 | Kesling | 433/18 |
| 3,775,850 | 12/1973 | Northcutt | 433/22 |
| 3,879,850 | 4/1975 | Wallshein | 433/18 |
| 3,913,228 | 10/1975 | Wallshein | 433/18 |
| 4,340,363 | 7/1982 | Klein et al. | 433/18 |
| 4,373,914 | 2/1983 | Colbert | 433/18 |
| 4,797,095 | 1/1989 | Armstrong et al. | 433/18 |

OTHER PUBLICATIONS

Brochure from "A" Company, Calif. (copyright 1986).

Primary Examiner—Cary E. Stone
Assistant Examiner—Adriene B. Lepiane
Attorney, Agent, or Firm—Gary L. Griswold; Walter N. Kirn; James D. Christoff

[57] ABSTRACT

A unitary, molded elastomeric wedge for rotating a tooth about its long axis during orthodontic treatment has a base which functions as a wedge portion, as well as two ligature loops connected to the base. In use, the loops cross over each other and function to ligate the archwire to the bracket while retaining the base in place. The wedge may be installed without removing the archwire from the bracket.

9 Claims, 1 Drawing Sheet

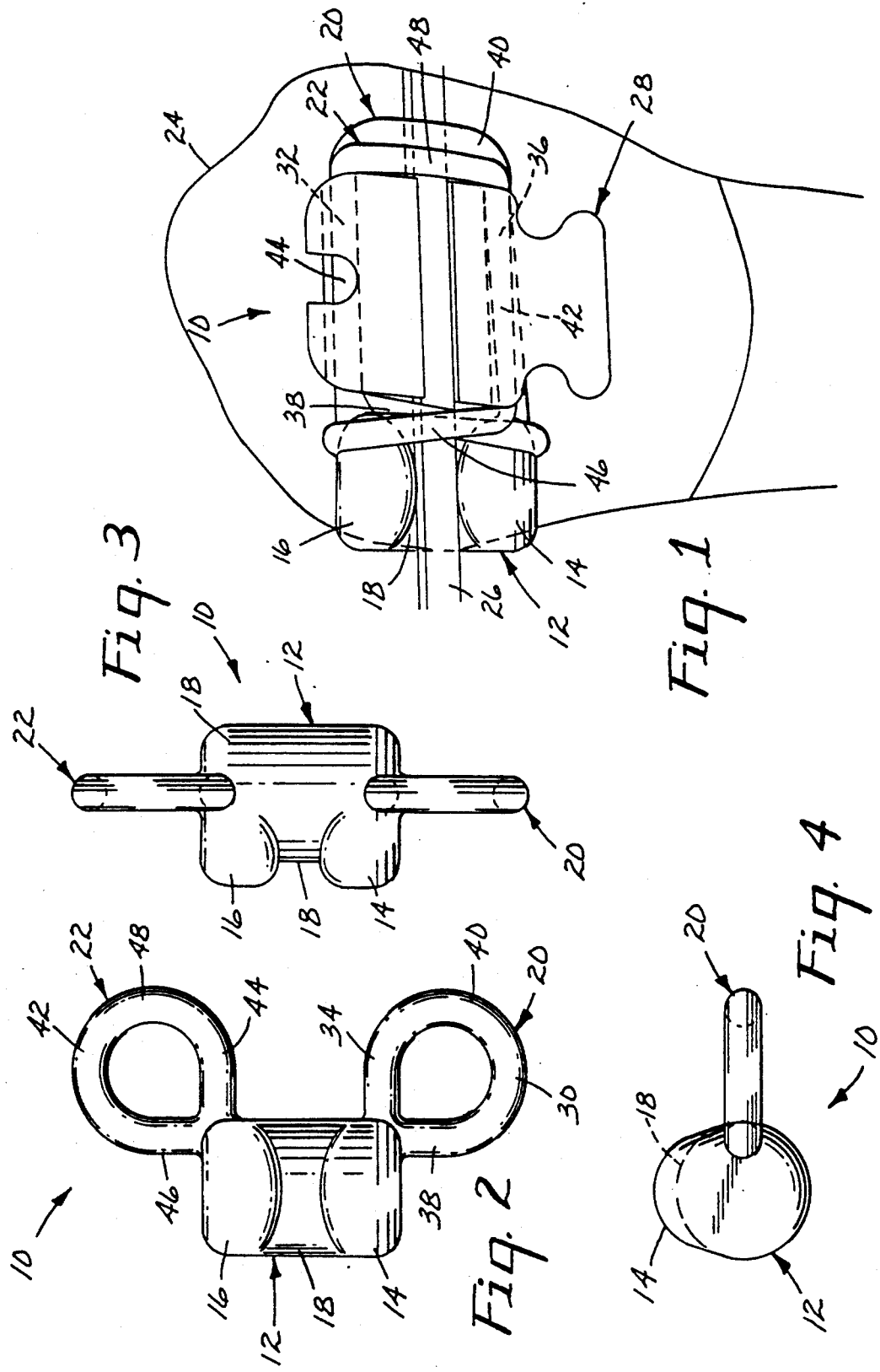

UNIVERSAL ORTHODONTIC ROTATION WEDGE

This is a continuation of application Ser. No. 07/282,434 filed Dec. 8, 1988, abandoned Oct. 12, 1990.

BACKGROUND OF THE INVENTION

1. Field of the Invention

This invention relates to a unitary elastomeric wedge for imparting an orthodontic rotational force to a tooth.

2. Description of the Related Art

Rotation wedges are often used during orthodontic treatment to rotate a tooth about its own long axis. Typically, rotation wedges are formed from an elastomeric material and are positioned adjacent the mesial or distal side of a bracket between the surface of the tooth and an archwire. The wedges are compressed when initially installed, and the inherent resiliency of the elastomeric material tends to rotate the tooth toward a desired orientation One type of rotation wedge known in the art is described in U.S. Pat. No. 4,340,363 and includes a wedge portion having a pair of spaced apart projections defining an archwire channel, as well as a planar portion with a pair of spaced apertures sized to receive one pair of tiewings of a standard twin orthodontic bracket. Another type of rotation wedge is described in U.S. Pat. No. 3,913,228 and includes a wedge portion that is integrally connected with a single loop adapted to be stretched somewhat when installed over two tiewings on one side of a twin bracket.

The aforementioned rotation wedges, however, cannot be placed in a position for use unless the archwire is first removed from the bracket to provide sufficient access to place the loop or apertures around the tiewings and behind a location to be subsequently occupied by the archwire. Moreover, once such wedges are in place, the orthodontist must then reposition the archwire and ligate the archwire to the bracket using a separate ligature tie or ring.

SUMMARY OF THE INVENTION

The present invention concerns an orthodontic rotation wedge having an elastomeric base of a size adapted to fit between an archwire and adjacent surfaces of a tooth. The wedge includes a pair of elastic ligature loops that are movable relative to each other and which are connected to the base for interconnecting the wedge as well as an archwire to an orthodontic bracket.

As a consequence, the wedge of the present invention can be placed into position between the archwire and the tooth, and the loops then stretched in opposite directions, each crossing over the other and encircling the entire bracket in the ligature grooves. The loops function to retain the wedge in place and also ligate the archwire to the bracket, all without disturbing the position of the archwire. A separate loop or ligature tie is unneccessary and a significant amount of the orthodontist's time is thereby spared.

BRIEF DESCRIPTION OF THE DRAWINGS

FIG. 1 is a front elevational view of a rotation wedge of the present invention, shown mounted in position between an archwire and a tooth with a pair of loops of the wedge extending around an adjacent orthodontic bracket;

FIG. 2 is a front elevational view of the wedge alone that is illustrated in FIG. 1 before installation, showing the loops in their normal orientation;

FIG. 3 is a side elevational view of the rotation wedge shown in FIG. 2; and

FIG. 4 is a bottom view of the wedge shown in FIGS. 2 and 3.

DESCRIPTION OF THE PREFERRED EMBODIMENT

An orthodontic rotation wedge is broadly designated by the numeral 10 in FIGS. 1–4 and is molded as a single piece from an elastomeric material suitable]e for oral environment and preferably colorless for aesthetic purposes. The wedge 10 includes a generally cylindrical base 12 which is integrally connected with a pair of spaced apart projections 14, 16 extending from opposite end portions of the base 12. The projections 14, 16 have opposed, curved facing surfaces that define therebetween an archwire channel 18.

A pair of ligature loops 20, 22 are integrally joined to opposite end portions of the same side of the base as shown, for example, in FIGS. 2 and 3, and normally lie in a reference plane which also contains the central axis of the cylindrical base 12. As illustrated, for example, in FIGS. 3 and 4, each of the loops 20, 22 has a thickness that is substantially less than the thickness of the base 12. One leg of each loop 20, 22 straightens somewhat and extends in a direction parallel to the central axis of base 12 toward the location of connection with the latter, while the other leg of each loop 20, 22 normally extends for a short distance in a straight direction parallel to respective ends of the base 12 adjacent the point of connection with the same. Each of the loops 20, 22 has a circular configuration in transverse section which is approximately one-half the cross-sectional area of conventional elastomeric ligatures. As shown in the drawings, the loops 20, 22 are connected to the base 12 at locations on opposite sides of the elongated channel 18.

FIG. 1 illustrates for exemplary purposes the wedge 10 as used to rotate a lower tooth 24 about its long axis during orthodontic treatment. Initially, the wedge 10 is positioned behind an archwire 26 at a location spaced from an orthodontic bracket 28 affixed to the tooth 24. Once the wedge 10 is moved to a position wherein the channel 18 receives the archwire 26 between projections 14, 16, the wedge 10 is then shifted in a direction along the length of the archwire 26 and toward the bracket 28 to the position shown in FIG. 1. As shown in FIG. 2, the spaced apart loops 20, 22 together with the base 12 present a recess for receiving the bracket 28.

Next, the lower loop 20 is stretched as needed to bring a normally lower section 30 of the loop 20 into an orientation extending along an upper ligature groove 32 formed in the bracket 28. At approximately the same time, a normally upper section 34 of the loop 20 is brought into an orientation extending along a lower ligature groove 36. Another section 38 of the loop 20 extends over the projection 14 as well as around the labial side of the archwire 26 adjacent the base 12, while a section 40 of the lower loop 20 extends between the ligature grooves 32, 36 and around the labial side of the archwire 26 on the opposite side of the bracket 28 remote from the base 12.

Subsequently, the upper loop 22 is stretched for installation until a normally upper section 42 of the loop 22 is received in the lower ligature groove 36 and a normally lower section 44 of the loop 22 is in place within the upper ligature groove 32. As depicted in FIG. 1, another section 46 of the loop 22 thus crosses over the upper projection 16 as well as the labial side of the lower loop section 38 and the archwire 26 on a side of the bracket 28 next to the base 12, while a section 48 of the upper loop 22 extends between the ligature grooves 32, 36 and over the labial side of the archwire 26.

As such, each of the loops 20, 22 completely encircle the bracket 28 and cross over each other to securely interconnect the wedge 10 as well as the archwire 26 to the bracket 28. The projections 14, 16 assist in retaining the base 12 in the position shown in FIG. 1 and generally prevent movement of the base 12 in an occlusal or gingival direction. The cross-sectional area of the loops 20, 22, being approximately one-half the cross-sectional area of conventional elastomeric ligatures, enables the loops 20, 22 to fully seat within the ligature grooves 32, 36 behind the tiewings of the bracket 28.

The base 12 has a diameter sufficiently large to ensure that the base 12 is in compression when placed between the archwire 26 and the adjacent surfaces of the tooth 24, so that the inherent resiliency of the material forming the base 12 urges the tooth 24 to rotate about its long axis toward a desired position. Moreover, the elastomeric material forming the wedge 10 enables the loops 20, 22 to be stretched sufficiently to encircle a variety of orthodontic brackets having differing configurations.

I claim:

1. An orthodontic rotation wedge for use with an orthodontic bracket having a ligature groove comprising:
   an elastomeric base having a side and a thickness adapted to fit in compression between an archwire and adjacent surfaces of a tooth; and
   a pair of elastic ligature loops each having a thickness substantially less than the thickness of said base, said loops being movable relative to each other and connected to said base for interconnecting said wedge as well as an archwire to the orthodontic bracket, said loops having cross-sectional areas for together fitting in the same ligature groove of the bracket, said loops being normally spaced apart from each other and extending from said side of said base, both of said loops together with said base presenting a recess for receiving said bracket.

2. The wedge of claim 1, wherein said base has opposite end portions, and each of said loops is connected to a respective one of said end portions.

3. The wedge of claim 1, wherein said base has a generally cylindrical configuration.

4. The wedge of claim 1; and including at least one projection which at least partially defines an archwire channel.

5. The wedge of claim 4, wherein said wedge has two spaced apart projections defining said archwire channel therebetween.

6. The wedge of claim 1, wherein said wedge is integrally molded from an elastomeric material.

7. The wedge of claim 1, wherein said base includes an archwire channel having an open top for free lateral reception of an archwire, and wherein said loops are connected to said base at locations ion opposite sides of said channel.

8. An orthodontic assembly comprising:
   an orthodontic bracket;
   an archwire; and
   a rotation wedge having an elastomeric base adapted to fit in compression between said archwire and adjacent surfaces of a tooth, said wedge including a pair of elastic ligature loops movable relative to each other and connected to said base, each of said ligature loops encircling said bracket and crossing over each other to securely interconnect said wedge as well as said archwire to said bracket.

9. The assembly of claim 8, wherein said base includes an archwire channel, and wherein said loops are connected to said base at locations on opposite sides of said channel.

* * * * *

UNITED STATES PATENT AND TRADEMARK OFFICE
CERTIFICATE OF CORRECTION

PATENT NO. : 5,044,946

DATED : September 3, 1991

INVENTOR(S) : James D. Cleary

It is certified that error appears in the above-identified patent and that said Letters Patent is hereby corrected as shown below:

Col. 1, line 21, after "orientation" insert -- . --.

Col. 2, line 13, "suitableje" should be -- suitable --.

Signed and Sealed this

Twenty-third Day of March, 1993

Attest:

STEPHEN G. KUNIN

*Attesting Officer*            *Acting Commissioner of Patents and Trademarks*